(12) United States Patent
Kupper et al.

(10) Patent No.: US 6,649,783 B2
(45) Date of Patent: Nov. 18, 2003

(54) SYNTHESIS OF (+/-)-2-((DIMETHYLAMINO)METHYL)-1-(ARYL)CYCLOHEXANOLS

(75) Inventors: Robert J. Kupper, East Greenwich, RI (US); Andreas Stumpf, Coventry, RI (US)

(73) Assignee: Euro-Celtique, S.A., Luxembourg (LU)

( * ) Notice: Subject to any disclaimer, the term of this patent is extended or adjusted under 35 U.S.C. 154(b) by 252 days.

(21) Appl. No.: 09/968,855

(22) Filed: Oct. 3, 2001

(65) Prior Publication Data

US 2003/0065221 A1 Apr. 3, 2003

(51) Int. Cl.$^7$ .......................... C07F 15/02; C07F 3/00; C07F 13/00; C09K 3/00; A61K 31/28
(52) U.S. Cl. .......................... 556/146; 556/45; 556/51; 556/113; 556/116; 556/118; 556/130; 556/135; 556/136; 556/150; 514/492; 514/494; 514/499; 514/501; 514/502; 252/183.13; 564/443
(58) Field of Search .......................... 556/45, 51, 113, 556/116, 118, 130, 135, 136, 146, 150; 252/183.13; 514/492, 494, 499, 501, 502

(56) References Cited

U.S. PATENT DOCUMENTS

| | | | |
|---|---|---|---|
| 3,652,589 A | 3/1972 | Flick et al. | 260/326.5 |
| 5,223,541 A | 6/1993 | Maryanoff et al. | 514/644 |
| 5,414,129 A | 5/1995 | Cherkez et al. | 564/425 |
| 5,672,755 A | 9/1997 | Lerman et al. | 564/425 |
| 5,723,668 A | 3/1998 | Buschmann et al. | 564/304 |
| 5,728,885 A | 3/1998 | Buschmann et al. | 564/304 |
| 5,801,201 A | 9/1998 | Graudums et al. | 514/646 |
| 5,874,620 A | 2/1999 | Lerman et al. | 564/443 |
| 5,877,351 A | 3/1999 | Anderson | 564/425 |

FOREIGN PATENT DOCUMENTS

| | | |
|---|---|---|
| EP | 0 831 082 | 3/1998 |
| EP | 0 778 262 | 4/1998 |
| EP | 0 940 385 | 9/1999 |
| GB | 997399 | 7/1965 |
| WO | WO 99/03820 | 1/1999 |
| WO | WO 99/36389 | 7/1999 |
| WO | WO 99/36390 | 7/1999 |
| WO | WO 99/61405 | 12/1999 |

OTHER PUBLICATIONS

Frankus, et al., "Über die Isomerentrennung, Strukturaufklärung und pharmakologische Charakterisierung von 1-(m-Methoxyphenyl)-2-(dimethylaminomethyl)-cyclohexan-1-ol," Arzneim.-Forsch./Drug Res. vol. 28 No. 1, pp. 114-121, 1978.

Itov et al. "A Practical Procedure for the Resolution of (+)-and (-)-Tramadol," Organic Process Research & Development, vol. 4, pp. 291-294, 2000.

Raffa et al., "Complementary and Synergistic Antinociceptive Interaction between the Enantiomers of Tramadol," The Journal of Pharmacology and Experimental Therapeutics, vol. 267, No. 1, pp. 331-340.

M.T. Reetz et al., "Unprecedented Stereoselectivity in the Addition of Organoiron (II) Reagents to Cyclohexanone Derivatives," *J. Chem. Soc., Chem. Comm.*, 3 328-330 (1993).

G.A. Molander et al., "Diastereoselective Addition of Organoytterbium Reagents to Carbonyl Substrates," *J. Org. Chem.*, 55:17 4990-4991 (1990).

Chem. Abstracts No. 35:47677 CA, Kharasch, "Factors Determining the COurse and Mechanism of Grignard Reactions. II The Effect of Metallic Compounds on the Reaction Between Isophorone and Methylmagnesium Bromide," *J. Amer. Chem. Soc., 63* 2308-2315 (1941).

*Primary Examiner*—Porfirio Nazario-Gonzalez
(74) *Attorney, Agent, or Firm*—Pennie & Edmonds LLP

(57) ABSTRACT

Compositions comprising (±)-2-((dimethylamino)methyl) cyclohexanone, a transition-metal salt, and an organic solvent and methods of preparing (±)-cis-2-((dimethylamino) methyl)-1-(aryl)cyclohexanols, in particular (±)-cis-2-((dimethylamino)methyl)-1-(3-methoxyphenyl) cyclohexanol, are disclosed herein. In one embodiment, the (±)-2-((dimethylamino)methyl)cyclohexanone and transition-metal salt are in the form of a (±)-2-((dimethylamino)methyl)cyclohexanone:transition-metal salt complex. In another embodimemt, aryl is 3-methoxyphenyl.

13 Claims, No Drawings

SYNTHESIS OF (+/-)-2-((DIMETHYLAMINO) METHYL)-1-(ARYL)CYCLOHEXANOLS

1. FIELD OF THE INVENTION

The present invention relates to compositions comprising (±)-2-((dimethylamino)methyl)cyclohexanone, a transition-metal salt, and an organic solvent and to methods for preparing (±)-cis-2-((dimethylamino)methyl)-1-(aryl) cyclohexanols, in particular, (±)-cis-2-((dimethylamino) methyl)-1-(3-methoxyphenyl) cyclohexanol.

2. BACKGROUND OF THE INVENTION

Tramadol, whose chemical name is (±)-cis-2-((dimethylamino)methyl)-1-(3-methoxyphenyl) cyclohexanol, is a non-addictive, non-opioid analgesic agent useful for the management of moderate to moderately severe pain. Tramadol does not cause side effects associated with opioid analgesic agents (R. B. Reffa, J. Pharmacol. Exp. Ther., 267, 331, (1993)). Tramadol hydrochloride compositions are sold under several trade names, including TRAMAL, ULTRAM, CRISPIN, and TRAMUNDIN.

Tramadol is racemic and consists of the following two enantiomers: (1R,2R)-2-((dimethylamino)methyl)-1-(3-methoxyphenyl)cyclohexanol (IIIb) and (1S,2S)-2-((dimethylamino)methyl)-1-(3-methoxyphenyl) cyclohexanol (IIIa). The chemical structures of these enantiomers are depicted below:

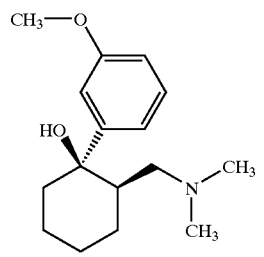

IIIa

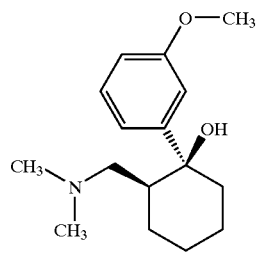

IIIb (±)-Trans-2-((dimethylamino)methyl)-1-(3-methoxyphenyl)cyclohexanol, tramadol's corresponding trans isomer, is also racemic and consists of the following two enantiomers: (1S,2R)-2-((dimethylamino)methyl)-1-(3-methoxyphenyl)cyclohexanol (IIIc) and (1R,2S)-2-((dimethylamino)methyl)-1-(3-methoxyphenyl) cyclohexanol (IIId). The chemical structures of these enantiomers are depicted below:

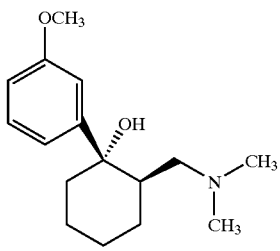

(IIIc)

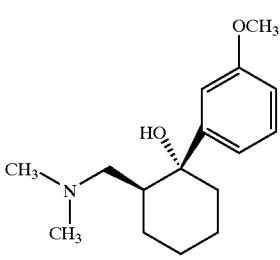

(IIId)

Tramadol may be formed from a Grignard reaction of (±)-2-((dimethylamino)methyl)cyclohexanone and 3-methoxyphenylmagnesium bromide (U.S. Pat. No. 3,652, 589 to Flick et al. and British Patent No. 997,399). But the product of this reaction is a mixture of tramadol and its corresponding trans isomer in a ratio of only about 78:22 to 82:18. Tramadol is significantly more analgesically active than its corresponding trans isomer (E. Frankus et al., Arzneim.-Forsch., 28(1A), 114 (1978)). Accordingly, tramadol is preferably separated from its corresponding trans isomer prior to administration.

The following paragraphs relate to processes for obtaining tramadol:

U.S. Pat. No. 3,652,589 to Flick et al. and British Patent No. 997,399 describe separating tramadol from its corresponding trans isomer by forming their corresponding hydrochloride salts and selectively crystallizing tramadol hydrochloride from moist dioxane. Dioxane, however, has many undesirable properties. For example, dioxane has recently been listed as a Category I carcinogen by OSHA (Kirk & Othmer, $3^{rd}$ Ed., Vol. 9, p. 3861), is known to cause central nervous system (CNS) depression and liver necrosis (ibid., Vol. 13, p. 2671), is flammable, and tends to form hazardous peroxides (ibid., Vol 17, p. 48).

U.S. Pat. No. 5,414,129 to Cherkez et al. discloses a selective precipitation of tramadol hydrochloride by treating a mixture of tramadol and its corresponding trans isomer with a solution of hydrochloric acid and a low molecular-weight alcohol or with gaseous hydrogen chloride in the presence of an organic solvent selected from medium-molecular-weight alcohols, ketones, esters, and ethers or aromatic ethers.

U.S. Pat. No. 5,672,755 to Lerman et al. and EP 0 778 262 disclose separating a mixture of tramadol and its corresponding trans isomer by reacting the mixture in a solvent at elevated temperature under acidic conditions. Under these conditions, tramadol's corresponding trans isomer is selectively dehydrated, and tramadol is precipitated as a salt.

U.S. Pat. No. 5,847,620 to Lerman et al. and EP 0 831 082 disclose separating a mixture of tramadol and its corresponding trans isomer by combining the mixture with an electrophilic reagent that selectively reacts with the hydroxyl group of tramadol's corresponding trans isomer and precipitating the unreacted tramadol from the reaction mixture.

U.S. Pat. No. 5,877,351 to Anderson discloses separating a mixture of tramadol and its corresponding trans isomer by adding aqueous HBr to the mixture. Here, tramadol hydrobromide selectively precipitates, while the hydrobromide of its corresponding trans isomer remains in solution.

U.S. Pat. No. 6,169,205 to Cabri et al. and EP 0 940 385 discloses a process for separating a mixture of tramadol and its corresponding trans isomer by selectively precipitating tramadol from a solution of water and a water-miscible organic solvent, such as acetone, dimethylformamide, ethanol, methanol, or tetrahydrofuran.

WO 99/36389 discloses a process for separating a mixture of tramadol and its corresponding trans isomer by diluting the mixture with a solvent and adding water to the resulting solution, forming hydrates of tramadol and its corresponding trans isomer. The hydrate of tramadol is then selectively precipitated.

WO 99/36390 discloses a process for separating a mixture of tramadol and its corresponding trans isomer by diluting the mixture with a solvent and contacting the resulting solution with hydrobromic or hydroiodic acid. The hydrobromic or hydroiodic salt of tramadol is then selectively precipitated.

WO 99/03820 discloses a process for separating a mixture of the monohydrate of tramadol and its corresponding trans isomer by selectively crystallizing tramadol monohydrate from ethyl acetate.

Conventional processes for preparing tramadol, which involve synthesizing a mixture of tramadol and its corresponding trans isomer via a Grignard reaction and selectively precipitating tramadol from the mixture, have disadvantages. In particular, about half of the reaction-mixture product, tramadol's corresponding trans isomer, is substantially less analgesically active then tramadol. Accordingly, a Grignard-reaction method that produces a high ratio of tramadol to its corresponding trans isomer is highly desirable.

WO 99/61405 discloses a process for preparing tramadol by reacting (±)-2-((dimethylamino)methyl)-1-(3-methoxyphenyl)cyclohexanone with 3-methoxyphenyl magnesium bromide in the presence of an amine or ether additive. The presence of the amine or ether additive allegedly increases the ratio of tramadol to its corresponding trans isomer.

There remains a need for methods for preparing tramadol having a high ratio of tramadol to its corresponding trans isomer.

3. SUMMARY OF THE INVENTION

The present invention is directed to a composition comprising (±)-2-((dimethylamino)methyl)cyclohexanone, a transition-metal salt and an organic solvent.

The present invention is further directed to a (±)-2-((dimethylamino)methyl)cyclohexanone:transition-metal salt complex.

The present invention is still further directed to a composition comprising the (±)-2-((dimethylamino)methyl)cyclohexanone:transition-metal salt complex and an organic solvent.

The (±)-2-((dimethylamino)methyl)cyclohexanone:transition-metal salt complex and the compositions of the invention are useful for synthesizing a (±)-cis-2-((dimethylamino)methyl)-1-(aryl)cyclohexanol and a (±)-trans-2-((dimethylamino)methyl)-1-(aryl)cyclohexanol in a ratio of at least about 85:15, wherein:

aryl is a phenyl or naphthyl group optionally substituted with one or more $R^1$ groups;

$R^1$ is selected from $C_1$–$C_{10}$ straight or branched chain alkyls, —$OR^2$, halogen, —$CF_3$, —$NH_2$, $NHR^2$, $NR^2R^2$, and each $R^2$ is independently a phenyl, benzyl or $C_1$–$C_{10}$ straight or branched alkyl group.

The invention is also directed to a method for synthesizing a (±)-cis-2-((dimethylamino)methyl)-1-(aryl)cyclohexanol and a (±)-trans-2-((dimethylamino)methyl)-1-(aryl)cyclohexanol in a ratio of at least about 85:15, comprising the steps of:

(a) contacting (1) a composition comprising (±)-2-((dimethylamino)methyl)cyclohexanone, a transition metal-salt, and an organic solvent and (2) an aryl organometallic compound to provide a (±)-cis-2-((dimethylamino)methyl)-1-(aryl)cyclohexoxide salt and a (±)-trans-2-((dimethylamino)methyl)-1-(aryl)cyclohexoxide salt in a ratio of at least about 85:15; and (b) protonating the (±)-cis-2-((dimethylamino)methyl)-1-(aryl)cyclohexoxide salt and (±)-trans-2-((dimethylamino)methyl)-1-(aryl)cyclohexoxide salt, wherein aryl is defined above.

The invention is further directed to a method for synthesizing a (±)-cis-2-((dimethylamino)methyl)-1-(aryl)cyclohexanol and a (±)-trans-2-((dimethylamino)methyl)-1-(aryl)cyclohexanol in a ratio of at least about 85:15, comprising the steps of:

(a) contacting (1) a composition comprising a (±)-2-((dimethylamino)methyl)cyclohexanone:transition metal-salt complex and an organic solvent and (2) an aryl organometallic compound to provide a (±)-cis-2-((dimethylamino)methyl)-1-(aryl)cyclohexoxide salt and a (±)-trans-2-((dimethylamino)methyl)-1-(aryl)cyclohexoxide salt in a ratio of at least about 85:15; and (b) protonating the (±)-cis-2-((dimethylamino)methyl)1-(aryl)cyclohexoxide salt and (±)-trans-2-((dimethylamino)methyl)-1-(aryl)cyclohexoxide salt, wherein aryl is defined above.

The invention is still further directed to a (±)-cis-2-((dimethylamino)methyl)-1-(aryl)cyclohexanol and a (±)-trans-2-((dimethylamino)methyl)-1-(aryl)cyclohexanol in a ratio of at least about 85:15, wherein aryl is defined above. A (±)-cis-2-((dimethylamino)methyl)-1-(aryl)cyclohexanol and a (±)-trans-2-((dimethylamino)methyl)-1-(aryl)cyclohexanol in a ratio of at least about 85:15 is useful for treating or preventing pain in a patient.

4. DETAILED DESCRIPTION OF THE INVENTION

The present invention is directed to compositions that are useful for preparing (±)-cis-2-((dimethylamino)methyl)-1-(aryl)cyclohexanols, in particular, tramadol. Tramadol is a (±)-cis-2-((dimethylamino)methyl)-1-(aryl)cyclohexanol, wherein aryl is 3-methoxyphenyl. The present invention is further directed to methods for preparing (±)-cis-2-((dimethylamino)methyl)-1-(aryl)cyclohexanols, in particular, tramadol, using the compositions of the invention.

4.1 Definitions

As used herein, the phrase "transition-metal salt" means the salt of a metal from group IB–VIIIB of the periodic table.

As used herein, the phrase "substantially anhydrous" means less than about 0.5 percent by weight, preferably less than about 0.25 by weight, and more preferably less than about 0.1 percent by weight of water.

As used herein the term "halogen" means —F, —Cl, —Br or —I.

As used herein, the term "halide" means chloride, bromide, iodide, or fluoride.

4.2 Transition-metal Salt Complexes of (±)-2-((Dimethylamino)methyl)cyclohexanone The compositions of the invention can comprise (±)-2-((dimethylamino)methyl)cyclohexanone, a transition-metal salt, and an organic solvent.

(±)-2-((Dimethylamino)methyl)cyclohexanone has the formula (I):

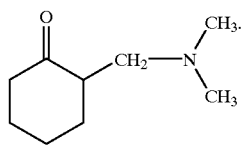

Compositions comprising (±)-2-((dimethylamino)methyl) cyclohexanone, a transition-metal salt, and an organic solvent can be prepared by contacting these components in any order. For example, the compositions of the invention can be prepared by adding (±)-2-((dimethylamino)methyl) cyclohexanone to an organic solvent followed by adding the transition-metal salt. Alternatively, the transition-metal salt can be added to the organic solvent followed by adding the (±)-2-((dimethylamino)methyl)cyclohexanone.

In one embodiment of the invention, the (±)-2-((dimethylamino)methyl)cyclohexanone and the transition-metal salt are present in the compositions of the invention in the form of a (±)-2-((dimethylamino)methyl) cyclohexanone:transition-metal salt complex. The formation of the complex can be demonstrated using spectroscopic techniques well known to those skilled in the art.

The concentration of (±)-2-((dimethylamino)methyl) cyclohexanone in the compositions of the invention generally ranges from about 0.001 to 20 moles/liter of organic solvent, preferably from about 0.01 to 10 moles/liter of organic solvent, and more preferably from about 0.1 to 1 moles/liter of organic solvent.

The transition-metal salt or its complex with (±)-2-((dimethylamino)methyl)cyclohexanone is present in the compositions of the invention in an amount of from about 0.01 to 5 mole percent, preferably from about 0.01 to 3 mole percent, and more preferably from about 0.01 to 1 mole percent, relative to the molar amount of (±)-2-((dimethylamino)methyl)cyclohexanone that is not complexed with the transition-metal salt.

Any transition-metal salt can be used in the compositions and methods of the invention. Transition metals useful for forming the transition-metal salt are copper, silver, gold, zinc, cadmium, mercury, scandium, yttrium, lanthanum, actinium, titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, and platinum. Preferred transition metals include tin, iron, copper, manganese, nickel, zinc, or a mixture thereof. The most preferred transition metal is iron. Any counterion can be used in the transition-metal salt including, but not limited to, halides; nitrate; sulfate; phosphate; cyanide; acyloxides, such as $C_1$–$C_{20}$ carboxylates, preferably $C_1$–$C_4$ carboxylates, more preferably acetate and trifluoroacetate; sulfonates, such as methanesulfonate, trifluoromethanesulfonate, benzenesulfonate, and toluenesulfonate; alkoxides, such as $C_1$–$C_{20}$ alkoxides, preferably $C_1$–$C_4$ alkoxides; aryloxides; and benzyloxides. Preferably, the counterion is a halide, more preferably, the counterion is chloride or bromide, and most preferably, the counterion is chloride.

Examples of suitable transition-metal salts include, but are not limited to, $ScX_3$, $FeX_2$, $FeX_3$, $FeX_4$, $FeX_6$, $SnX_4$, $SnX_2$, $ZnX_2$, $CoX_2$, $CoX_3$, $NiX_2$, $CuX$, $CuX_2$, $TiX_2$, $TiX_3$, $TiX_4$, $MnX_2$, $MnX_3$, $MnX_4$, $MnX_6$, $MnX_7$, $HgX$, $HgX_2$, $VX_2$, $VX_3$, $VX_4$, $VX_5$, $CrX_2$, $CrX_3$, $CrX_4$, $CrX_5$, $CrX_6$, $YX_3$, $ZrX_3$, $ZrX_4$, $NbX_3$, $NbX_4$, $NbX_5$, $MoX_3$, $MoX_4$, $MoX_5$, $MoX_6$, $TcX_4$, $TcX_6$, $RuX_3$, $RuX_4$, $RuX_5$, $RuX_6$, $RhX_3$, $RhX_5$, $RhX_6$, $PdX_2$, $AgX$, $AgX_2$, $AgX_3$, $CdX_2$, $LaX_3$, $HfX_3$, $HfX_4$, $TaX_3$, $TaX_4$, $TaX_5$, $WX_3$, $WX_4$, $WX_5$, $WX_6$, $ReX_2$, $ReX_3$, $ReX_4$, $ReX_5$, $ReX_6$, $ReX_7$, $OsX_3$, $OsX_4$, $OsX_5$, $OsX_6$, $IrX_3$ $IrX_5$, $IrX_6$, $PtX_2$, $PtX_3$, $PtX_4$, $PtX_5$, $PtX_6$, $AuX$, $AuX_3$, $AuX_5$, and mixtures thereof, wherein X is a counterion, including those listed above, preferably a halide, more preferably chloride or bromide, and most preferably chloride. Accordingly, preferred transition-metal salts are tin halides, iron halides, manganese halides, copper halides, nickel halides, and zinc halides. The most preferred transition-metal salt is ferric chloride.

Organic solvents suitable for use in the compositions and methods of the invention include, but are not limited to, benzene, toluene, xylene, pentane, heptane, hexane, cyclohexane, ligroin, petroleum ether, diethyl ether, tetrahydrofuran, dioxane, and mixtures thereof. Preferred solvents include tetrahydrofuran and diethyl ether. Preferably the solvents are substantially anhydrous.

4.3 Methods for Synthesizing (±)-2-(Dimethylamino)methyl)-1-(aryl)cyclohexanols To provide a (±)-cis-2-((dimethylamino)methyl)-1-(aryl) cyclohexanol and a (±)-trans-2-((dimethylamino)methyl)-1-(aryl)cyclohexanol in a ratio of at least about 85:15, the compositions of the invention can advantageously be contacted with the aryl organometallic compound.

The aryl organometallic compound has one or more aryl groups chemically bonded to one or more metals, M, and can further have one or more counterions, X, to balance the charge on M, wherein aryl is a phenyl or naphthyl group optionally substituted with one or more $R^1$ groups;

$R^1$ is selected from $C_{1-C10}$ straight or branched chain alkyls, —$OR^2$, halogen, —$CF_3$, —$NH_2$, $NHR^2$, $NR^2R^2$; and each $R^2$ is independently a phenyl, benzyl or a $C_1$–$C_{10}$ straight or branched alkyl group.

Preferably, one or more of the $C_1$–$C_{10}$ straight or branched chain alkyl groups, when present, is a $C_1$–$C_4$ straight or branched chain alkyl group.

Preferably, the phenyl or naphthyl group is substituted with an —$OR^2$ group, wherein $R^2$ is a phenyl, benzyl, or a $C_1$–$C_4$ straight or branched chain alkyl group. More preferably, the aryl is phenyl and substituted with an —$OCH_3$ group. Most preferably the aryl is substituted at its 3-position.

The aryl organometallic compounds useful in the invention can be made by reacting the aryl organometallic compound's corresponding aryl halide with M according to well-known procedures. Methods of synthesizing aryl halides are well known to those skilled in the art. Alternatively, the aryl halides can be obtained commercially, for example from Diaz Chemical Corp., Holley, N.Y.

Any M known to those skilled in the art can be used in the aryl organometallic compound (For example, see, Fieser's Reagents for Organic Synthesis, Wiley; and Organometallics in Synthesis: A Manual, M. Schlosser, ed., Wiley, 1st. ed., 1994). Preferably, M is magnesium, lithium, potassium, sodium, zinc, lead, mercury, copper, manganese, or a mixture thereof. X in the organometallic compound can be any of the counterions discussed above. When the aryl halide is substituted with one or more —$NH_2$ or —$NHR^2$ groups, then an excess of M is preferred.

The (±)-cis-2-((dimethylamino)methyl)-1-(aryl) cyclohexanol and (±)-trans-2-((dimethylamino)methyl)-1-(aryl)cyclohexanol are obtained by the present methods in a ratio of at least about 85:15, preferably at least about 90:10, more preferably at least about 92:8, even more preferably at least about 94:6, even more preferably at least about 98:2, and most preferably at least about 99:1. Without being bound by any theory, Applicants believe that the transition-metal salt, optionally in the form of a (±)-2-((dimethylamino)methyl)cyclohexanone:transition-metal salt complex, is responsible for catalyzing the formation of the (±)-cis-2-((dimethylamino)methyl)-1-(aryl) cyclohexanol and (±)-trans-2-((dimethylamino)methyl)-1-(aryl)cyclohexanol in a ratio of at least about 85:15.

A (±)-cis-2-((dimethylamino)methyl)-1-(aryl) cyclohexanol is a racemic mixture of two enantiomers having the structure of (IIa) and (IIb), wherein aryl is defined above:

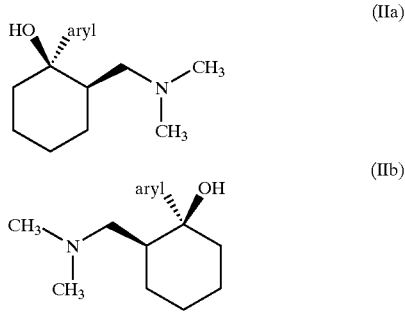

(IIa)

(IIb)

A (±)-Trans-2-((dimethylamino)methyl)-1-(aryl) cyclohexanol is a racemic mixture of two enantiomers having the structure of (IIc) and (IId), wherein aryl is defined above:

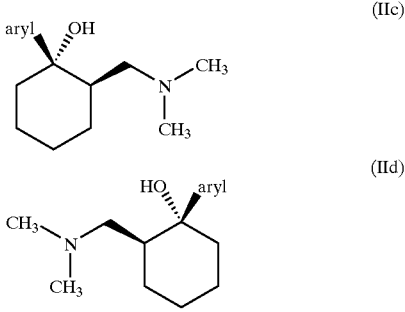

(IIc)

(IId)

The invention is further directed to methods for preparing a (±)-cis-2-((dimethylamino)methyl)-1-(aryl)cyclohexanol and a (±)-trans-2-((dimethylamino)methyl)-1-(aryl)cyclohexanol in a ratio of at least about 85:15, comprising the steps of:

(a) contacting (1) a composition comprising (±)-2-((dimethylamino)methyl)cyclohexanone, a transition metal-salt, and an organic solvent and (2) an aryl organometallic compound to provide a (±)-cis-2-((dimethylamino)methyl)-1-(aryl)cyclohexoxide salt and a (±)-trans-2-((dimethylamino)methyl)-1-(aryl) cyclohexoxide salt in a ratio of at least about 85:15; and (b) protonating the (±)-cis-2-((dimethylamino)methyl)-1-(aryl)cyclohexoxide salt and the (±)-trans-2-((dimethylamino)methyl)-1-(aryl)cyclohexoxide salt, wherein aryl is defined above.

A composition of the invention can be added to the aryl organometallic compound or the aryl organometallic compound can be added to a composition of the invention. Advantageously, the aryl organometallic compound is in the presence of one or more organic solvents, described above, when contacted with a composition of the invention. When the aryl organometallic compound is in the presence of an organic solvent, the aryl organometallic compound is preferably suspended or dissolved in the organic solvent. Preferably, a composition of the invention is added to the aryl organometallic compound in the presence of an organic solvent described above. Generally, a composition of the invention and the aryl organometallic compound are contacted over a period of at least about 30 minutes, preferably at least about 1 hour, and more preferably at least about 2 hours, and most preferably at least about 4 hours. When the aryl organometallic compound is in the presence of an organic solvent when contacted with a composition of the invention, the organic solvent of the composition of the invention and the organic solvent that the aryl organometallic compound is in the presence of are preferably the same.

The aryl organometallic compound can be prepared by known methods (for example, see, Fieser's Reagents for Organic Synthesis, Wiley; and Organometallics in Synthesis: A Manual, M. Schlosser, ed., Wiley, 1st. ed., 1994). When M is magnesium or lithium, for example, the aryl organometallic compound can be prepared by adding $Mg^0$ or $Li^0$, preferably in the form of small pieces, to an organic solvent and adding an aryl halide, preferably an aryl chloride, bromide, or iodide, where aryl is defined above (For example, see, U.S. Pat. No. 3,652,589 to Flick et al.; U.S. Pat. No. 5,877,351 to Anderson). Preferably, the organic solvent is substantially anhydrous. Preferably, the amount of the aryl halide added to the organic solvent is an amount sufficient to provide a final concentration of the aryl organometallic compound that is from about 0.01 to about 20 moles/liter of organic solvent, preferably from about 0.1 to about 10 moles/liter of organic solvent, and more preferably from about 0.5 to about 5 moles/liter of organic solvent. Preferably, M is present in an amount of about 1 to 1.5 molar equivalents, preferably about 1 to 1.3 molar equivalents, and more preferably about 1 to 1.1 molar equivalents relative to the aryl halide. Preferred M are lithium and magnesium, with lithium being the most preferred.

Suitable solvents for preparing the aryl organometallic compound include those organic solvents described above. Preferred solvents include tetrahydrofuran and diethyl ether.

Preferably, the aryl organometallic compound is contacted with a composition of the invention in an amount of from about 1 to about 1.5 molar equivalents, preferably from about 1 to about 1.3 molar equivalents, and more preferably from about 1 to about 1.1 molar equivalents relative to the (±)-2-((dimethylamino)methyl)cyclohexanone.

A composition of the invention and the aryl organometallic compound are preferably contacted at a temperature of between from about −78° C. and about the boiling point of the organic solvent. The contacting can be performed at a temperature of from about −78° C. to about 25° C., preferably from about −78° C. to about 0° C., more preferably from about −25° C. to about −78° C., and most preferably from about −50° C. to about −78° C. Performing the contacting at lower temperatures can reduce or eliminate a side reaction or the formation of any impurity.

After a composition of the invention and the aryl organometallic compound are contacted they can be allowed to react for a time period of from about 15 minutes to about 24 hours, preferably from about 1 hour to about 12 hours, and most preferably from about 2 hours to about 6 hours. Typical reaction temperatures are the same as the contacting temperatures, described above. The progress of the resulting reaction can be monitored using a conventional analytical technique, including, but are not limited to, thin-layer chromatography (TLC), high-performance liquid chromatography (HPLC), gas chromatography (GC), and nuclear magnetic resonance spectroscopy (NMR) such as $^1$H and $^{13}$C NMR.

Reaction of a composition of the invention and the aryl organometallic compound provides the (±)-cis-2-((dimethylamino)methyl)-1-(aryl)cyclohexoxide salt and (±)-trans-2-((dimethylamino)methyl)-1-(aryl)cyclohexoxide salt in a ratio of at least about 85:15, preferably at least about 90:10, more preferably at least about 92:8, even more preferably at least about 94:6, even more preferably at least about 98:2, and most preferably at least about 99:1. The counterion of the (±)-cis-2-((dimethylamino)methyl)-1-(aryl)cyclohexoxide salt and (±)-trans-2-((dimethylamino)methyl)-1-(aryl)cyclohexoxide salt is M and any associated X.

The (±)-cis-2-((dimethylamino)methyl)-1-(aryl)cyclohexoxide salt and (±)-trans-2-((dimethylamino)methyl)-1-(aryl)cyclohexoxide salt in a ratio of at least about 85:15 is protonated to provide a (±)-cis-2-((dimethylamino)methyl)-1-(aryl)cyclohexanol and (±)-trans-2-((dimethylamino)methyl)-1-(aryl)cyclohexanol in a ratio of at least about 85:15, preferably at least about 90:10, more preferably at least about 92:8, even more preferably at least about 94:6, even more preferably at least about 98:2, and most preferably at least about 99:1. It will be understood that protonating the (±)-cis-2-((dimethylamino)methyl)-1-(aryl)cyclohexoxide salt and (±)-trans-2-((dimethylamino)methyl)-1-(aryl)cyclohexoxide salt does not significantly affect the ratio of the resulting (±)-cis-2-((dimethylamino)methyl)-1-(aryl)cyclohexanol and (±)-trans-2-((dimethylamino)methyl)-1-(aryl)cyclohexanol.

Standard techniques can be used to protonate the (±)-cis-2-((dimethylamino)methyl)-1-(aryl)cyclohexoxide salt and (±)-trans-2-((dimethylamino)methyl)-1-(aryl)cyclohexoxide salt. Any acid can be used to protonate the (±)-cis-2-((dimethylamino)methyl)-1-(aryl)cyclohexoxide salt and (±)-trans-2-((dimethylamino)methyl)-1-(aryl)cyclohexoxide salt. Preferred acids include, but are not limited to, hydrochloric acid, hydrobromic acid, hydroiodic acid, hydrofluoric acid, phosphoric acid, sulfuric acid, nitric acid, acetic acid, citric acid, trifluoromethanesulfonic acid, p-toluenesulfonic acid, benzenesulfonic acid, ethanesulfonic acid, methanesulfonic acid, oxalic acid, malic acid, lactic acid, salicylic acid, oleic acid, tartaric acid, ascorbic acid, succinic acid, fumaric acid, gluconic acid, formic acid, and benzoic acid.

In one embodiment, an acid is added to a reaction mixture comprising the (±)-cis-2-((dimethylamino)methyl)-1-(aryl)cyclohexoxide salt and (±)-trans-2-((dimethylamino)methyl)-1-(aryl)cyclohexoxide salt to facilitate purification. Here, the final pH of the reaction mixture is maintained at a sufficiently high value to avoid protonation of the amino group of the (±)-cis-2-((dimethylamino)methyl)-1-(aryl)cyclohexanol and (±)-trans-2-((dimethylamino)methyl)-1-(aryl)cyclohexanol.

Preferably, the (±)-cis-2-((dimethylamino)methyl)-1-(aryl)cyclohexoxide and (±)-trans-2-((dimethylamino)methyl)-1-(aryl)cyclohexoxide are protonated with water.

In another embodiment, a salt, preferably a pharmaceutically acceptable salt, the (±)-cis-2-((dimethylamino)methyl)-1-(aryl)cyclohexanol and (±)-trans-2-((dimethylamino)methyl)-1-(aryl)cyclohexanol in a ratio of at least about 85:15 is obtained in isolated and purified form as described below.

The (±)-cis-2-((dimethylamino)methyl)-1-(aryl)cyclohexanol and (±)-trans-2-((dimethylamino)methyl)-1-(aryl)cyclohexanol in a ratio of at least about 85:15 can be isolated and purified. In one embodiment, the (±)-cis-2-((dimethylamino)methyl)-1-(aryl)cyclohexanol and (±)-trans-2-((dimethylamino)methyl)-1-(aryl)cyclohexanol in a ratio of at least about 85:15 are isolated and purified from a chemical reaction mixture. As used herein, "isolated" means that the (±)-cis-2-((dimethylamino)methyl)-1-(aryl)cyclohexanol and (±)-trans-2-((dimethylamino)methyl)-1-(aryl)cyclohexanol in a ratio of at least about 85:15 is separated from other components of a reaction mixture. Preferably, via conventional techniques, the (±)-cis-2-((dimethylamino)methyl)-1-(aryl)cyclohexanol and (±)-trans-2-((dimethylamino)methyl)-1-(aryl)cyclohexanol in a ratio of at least about 85:15 is purified. As used herein, "purified" means that when isolated, the isolate contains at least about 90%, preferably at least about 95%, more preferably at least about 98% of the (±)-cis-2-((dimethylamino)methyl)-1-(aryl)cyclohexanol and the (±)-trans-2-((dimethylamino)methyl)-1-(aryl)cyclohexanol in a ratio of at least about 85:15 by weight of the isolate. Isolation and purification can be achieved using procedures well known to those skilled in the art including, for example, but not limited to, extraction, recrystallization, column chromatography, sublimation, preparative TLC, preparative HPLC, and preparative GC. Representative processes for isolating and purifying or increasing the ratio of the (±)-cis-2-((dimethylamino)methyl)-1-(aryl)cyclohexanol and (±)-trans-2-((dimethylamino)methyl)-1-(aryl)cyclohexanol in a ratio of at least about 85:15 are described in, for example, U.S. Pat. No. 6,169,205 to Cabri et al., U.S. Pat. Nos. 5,723,668 and 5,728,885 to Buschmann et al., U.S. Pat. Nos. 5,672,755 and 5,874,620 to Lerman et al., U.S. Pat. No. 5,414,129 to Cherkez et al., U.S. Pat. No. 5,877,351 to Anderson, WO 99/36389, WO 99/36390, WO 99/61405, WO 99/03820, EP 0 940 385, EP 0 831 082, and EP 0 778 262.

In one embodiment, the (±)-cis-2-((dimethylamino)methyl)-1-(aryl)cyclohexanol can be separated from the (±)-trans-2-((dimethylamino)methyl)-1-(aryl)cyclohexanol using standard techniques and/or the methods disclosed herein. Once separated, the (±)-cis-2-((dimethylamino)methyl)-1-(aryl)cyclohexanol or (±)-trans-2-((dimethylamino)methyl)-1-(aryl)cyclohexanol can be separated into its individual enantiomers according to the methods of U.S. Pat. No. 5,723,668 to Buschmann et al.

In another embodiment, the (±)-cis-2-((dimethylamino)methyl)-1-(aryl)cyclohexanol and (±)-trans-2-((dimethylamino)methyl)-1-(aryl)cyclohexanol in a ratio of at least about 85:15 are converted to amine salt and then isolated and purified as the salt. For example, the hydrochloride salt of the (±)-cis-2-((dimethylamino)methyl)-1-

(aryl)cyclohexanol and (±)-trans-2-((dimethylamino) methyl)-1-(aryl)cyclohexanol in a ratio of at least about 85:15 can be recrystallized from acetonitrile, then from isopropanol to remove residual acetonitrile as disclosed in WO 99/61405. Where aryl is 3-methoxyphenyl, tramadol can be purified according to the procedures described in U.S. Pat. No. 5,874,620 to Lerman et al. A (±)-cis-2-((dimethylamino)methyl)-1-(aryl)cyclohexanol and (±)-trans-2-((dimethylamino)methyl)-1-(aryl)cyclohexanol in a ratio of at least about 85:15, preferably that which is isolated and purified, can be administered to a patient to treat or prevent pain and is useful for preparing pharmaceutical compositions.

Preferably, the overall yield of the isolated and purified (±)-cis-2-((dimethylamino)methyl)-1-(aryl)cyclohexanol and (±)-trans-2-((dimethylamino)methyl)-1-(aryl) cyclohexanol in a ratio of at least about 85:15 is greater than about 50 percent, more preferably greater than about 75 percent, and most preferably greater than about 80 percent based on the molar equivalents of the starting materials.

The (±)-cis-2-((dimethylamino)methyl)-1-(aryl) cyclohexanol and (±)-trans-2-((dimethylamino)methyl)-1-(aryl)cyclohexanol in a ratio of at least about 85:15 can be converted to a pharmaceutically acceptable salt by protonating the nitrogen atom of the (±)-cis-2-((dimethylamino) methyl)-1-(aryl)cyclohexanol and (±)-trans-2-((dimethylamino)methyl)-1-(aryl)cyclohexanol with an acid capable of forming a pharmaceutically acceptable salt.

The phrase "pharmaceutically acceptable salt(s)," as used herein includes, but are not limited to, salts of the basic nitrogen group that is present in the (±)-cis-2-((dimethylamino)methyl)-1-(aryl)cyclohexanol and (±)-trans-2-((dimethylamino)methyl)-1-(aryl)cyclohexanol in a ratio of at least about 85:15. (±)-Cis-2-((dimethylamino) methyl)-1-(aryl)cyclohexanol and (±)-trans-2-((dimethylamino)methyl)-1-(aryl)cyclohexanol in a ratio of at least about 85:15 are capable of forming a wide variety of salts with various inorganic and organic acids. The acids that can be used to prepare pharmaceutically acceptable acid addition salts are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. The (±)-cis-2-((dimethylamino)methyl)-1-(aryl)cyclohexanol and (±)-trans-2-((dimethylamino)methyl)-1-(aryl)cyclohexanol in a ratio of at least about 85:15 can also form pharmaceutically acceptable salts with various amino acids, in addition to the acids mentioned above. Preferably, the pharmaceutically acceptable salt is a hydrochloride salt.

Methods for forming pharmaceutically acceptable salts are well known to those skilled in the art. In particular, the hydrochloride salt can be prepared by treating the (±)-cis-2-((dimethylamino)methyl)-1-(aryl)cyclohexanol and (±)-trans-2-((dimethylamino)methyl)-1-(aryl)cyclohexanol in a ratio of at least about 85:15 with, for example, gaseous HCl in ether, tetrahydrofuran, acetonitrile, or ethanol. Salts of the (±)-cis-2-((dimethylamino)methyl)-1-(aryl)cyclohexanol and (±)-trans-2-((dimethylamino)methyl)-1-(aryl) cyclohexanol in a ratio of at least about 85:15 can be administered to a patient to treat or prevent pain and are useful for preparing pharmaceutical compositions.

In a specific embodiment, the aryl organometallic compound is 3-methoxyphenyllithium. In another specific embodiment, the aryl organometallic compound is 3-methoxyphenylmagnesium chloride, bromide, or iodide.

In the above methods the ratio of the (±)-cis-2-((dimethylamino)methyl)-1-(aryl)cyclohexanol to the (±)-trans-2-((dimethylamino)methyl)-1-(aryl)cyclohexanol can be determined spectroscopically, for example, using HPLC as described in WO 99/61405.

4.5 Therapeutic/Prophylactic Administration and Compositions Comprising (±)-2-(Dimethylamino) methyl)-1-(Aryl)cyclohexanols Due to the activity of the (±)-cis-2-((dimethylamino) methyl)-1-(aryl)cyclohexanol and (±)-trans-2-((dimethylamino)methyl)-1-(aryl)cyclohexanol in a ratio of at least about 85:15, or a pharmaceutically acceptable salt thereof, they are advantageously useful in veterinary and human medicine. For example, a (±)-cis-2-((dimethylamino) methyl)-1-(aryl)cyclohexanol and (±)-trans-2-((dimethylamino)methyl)-1-(aryl)cyclohexanol in a ratio of at least about 85:15, or a pharmaceutically acceptable salt thereof, are useful for preparing pharmaceutical compositions ("the pharmaceutical compositions") for the treatment or prevention of pain.

The pharmaceutical compositions comprise an effective amount of a (±)-cis-2-((dimethylamino)methyl)-1-(aryl) cyclohexanol and a (±)-trans-2-((dimethylamino)methyl)-1-(aryl)cyclohexanol in a ratio of at least about 85:15, or a pharmaceutically acceptable salt thereof, preferably in isolated and purified form, preferably, together with a suitable amount of a pharmaceutically acceptable carrier so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the (±)-cis-2-((dimethylamino)methyl)-1-(aryl) cyclohexanol and (±)-trans-2-((dimethylamino)methyl)-1-(aryl)cyclohexanol in a ratio of at least about 85:15, or a pharmaceutically acceptable salt thereof, is administered. Such pharmaceutical carriers can be liquids, such as water and oils, including those of petroleum, animal, vegetable or synthetic origin, such as peanut oil, soybean oil, mineral oil, sesame oil, and the like. The pharmaceutical carriers can be saline, gum acacia, gelatin, starch paste, talc, keratin, colloidal silica, urea, and the like. In addition, auxiliary, stabilizing, thickening, lubricating and coloring agents may be used. When administered to a patient, the (±)-cis-2-((dimethylamino)methyl)-1-(aryl)cyclohexanol and (±)-trans-2-((dimethylamino)methyl)-1-(aryl)cyclohexanol in a ratio of at least about 85:15, or a pharmaceutically acceptable salt thereof, and pharmaceutically acceptable carriers are preferably sterile. Water is a preferred carrier when the (±)-cis-2-((dimethylamino)methyl)-1-(aryl)cyclohexanol and (±)-trans-2-((dimethylamino)methyl)-1-(aryl) cyclohexanol in a ratio of at least about 85:15, or a pharmaceutically acceptable salt thereof, is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable carrier is a capsule (see e.g., U.S. Pat. No. 5,698,155). Other examples of suitable pharmaceutical carriers are described in "Remington's Pharmaceutical Sciences" by E. W. Martin.

In a preferred embodiment, the pharmaceutical compositions are formulated in accordance with routine procedures as a pharmaceutical composition adapted for intravenous administration to human beings. Preferably, the pharmaceutical compositions for intravenous administration are solutions in sterile isotonic aqueous buffer. Where necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical compositions are to be administered by infusion, they can be dispensed, for example, with an infusion bottle containing sterile pharmaceutical grade water or saline. Where the pharmaceutical compositions are administered by injection, an ampoule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered pharmaceutical compositions. In these later platforms, fluid from the environment surrounding the capsule is imbibed by the driving compound, which swells to displace the agent or agent composition through an aperture. These delivery platforms can provide an essentially zero-order delivery profile as opposed to the spiked profiles of immediate release formulations. A time delay material such as glycerol monostearate or glycerol stearate may also be used. Oral compositions can include standard carriers such as mannitol, lactose, starch, magnesium stearate, sodium saccharine, cellulose, magnesium carbonate, etc. Such carriers are preferably of pharmaceutical grade.

The amount of the (±)-cis-2-((dimethylamino)methyl)-1-(aryl)cyclohexanol and (±)-trans-2-((dimethylamino)methyl)-1-(aryl)cyclohexanol in a ratio of at least about 85:15, or a pharmaceutically acceptable salt thereof, that will be effective in the treatment or management of pain will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disorder, and should be decided according to the judgment of the practitioner and each patient's circumstances. Oral compositions preferably contain 10% to 95% of the (±)-cis-2-((dimethylamino)methyl)-1-(aryl)cyclohexanol and (±)-trans-2-((dimethylamino)methyl)-1-(aryl)cyclohexanol in a ratio of at least about 85:15. Effective doses can be developed from dose-response curves derived from in vitro or animal model test systems. Such animal models and systems are well known in the art.

Preferably, pharmaceutical compositions for treating or preventing pain in a patient comprise from about 0.1 to about 800 mg/kg, preferably from about 0.3 to about 200 mg/kg, and more preferably from about 1 to about 100 mg/kg, per body weight of the (±)-cis-2-((dimethylamino)methyl)-1-(aryl)cyclohexanol and (±)-trans-2-((dimethylamino)methyl)-1-(aryl)cyclohexanol, or a pharmaceutically acceptable salt thereof, in a ratio of at least about 85:15. The pharmaceutical compositions can be administered at a daily dosage of from about 10 to 6000 mg/kg/day.

When administered to a patient, e.g., an animal for veterinary use or to a human for clinical use, the (±)-cis-2-((dimethylamino)methyl)-1-(aryl)cyclohexanol and (±)-trans-2-((dimethylamino)methyl)-1-(aryl)cyclohexanol in a ratio of at least about 85:15, or a pharmaceutically acceptable salt thereof, is preferably in an isolated and purified form. The patient is preferably an animal, including, but not limited, to an animal such a cow, horse, sheep, pig, chicken, turkey, quail, cat, dog, mouse, rat, rabbit, guinea pig, etc., and is more preferably a mammal, and most preferably a human.

The pharmaceutical compositions can be administered by any convenient route, for example by infusion or bolus injection, by absorption through epithelial or mucocutaneous linings (e.g., oral mucosa, rectal and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer the pharmaceutical compositions. In certain embodiments, more than one (±)-cis-2-((dimethylamino)methyl)-1-(aryl)cyclohexanol and (±)-trans-2-((dimethylamino)methyl)-1-(aryl)cyclohexanol in a ratio of at least about 85:15, or a pharmaceutically acceptable salt thereof, is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically to the ears, nose, eyes, or skin. The preferred mode of administration is oral, but other modes of administration can be left to the discretion of the practitioner.

In specific embodiments, it may be desirable to administer the pharmaceutical compositions locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In certain embodiments, it may be desirable to introduce the pharmaceutical compositions into the central nervous system by any suitable route, including intraventricular and intrathecal injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the pharmaceutical compositions can be formulated as a suppository, with traditional binders and carriers such as triglycerides.

In another embodiment, the pharmaceutical compositions can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.).

In yet another embodiment, the pharmaceutical compositions can be delivered in a controlled-release system. In one embodiment, a pump can be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled-release system can be placed in proximity of the target of the pharmaceutical compositions, thus requiring only a fraction of the systemic dose (see, e.g., Goodson, in Medical Applications of Controlled Release, supra, vol. 2, pp. 115–138 (1984)). Other controlled-release systems discussed in the review by Langer (Science 249:1527–1533 (1990)) can be used.

The invention also provides pharmaceutical packs or kits comprising one or more containers filled with one or more (±)-cis-2-((dimethylamino)methyl)-1-(aryl)cyclohexanol and (±)-trans-2-((dimethylamino)methyl)-1-(aryl) cyclohexanol in a ratio of at least about 85:15, or a pharmaceutically acceptable salt thereof. Optionally associated with such container(s) can be a notice in the form prescribed by a governmental agency regulating the manufacture, use or sale of pharmaceuticals or biological products, which notice reflects approval by the agency of manufacture, use or sale for human administration.

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

5. EXAMPLES

Example 1
Synthesis of a Mixture of Tramadol and its Corresponding Trans Isomer in a Ratio of About 94:6

To 120 mL of anhydrous tetrahydrofuran (THF) cooled to −50° C. was added 400 mL of sec-butyl lithium (0.52 mol, 1.3 M solution in cyclohexane). The resulting yellow suspension was stirred for 10 min and then 63.56 g of neat 3-bromoanisole (0.34 mol) was added dropwise with stirring. The yellow suspension turned red, and then a white precipitate formed. The resulting white suspension was stirred for 30 min. In a separate vessel 52.75 g of (±) 2-((dimethylamino)methyl) cyclohexanone was dissolved in 107 mL of anhydrous THF at 0° C. To the resulting solution of (±) 2-((dimethylamino)methyl) cyclohexanone was added, dropwise with stirring, a solution of 1.03 g of iron (III) chloride (6.3 mmol, 1 mol percent) in anhydrous THF. The resulting violet solution was transferred dropwise to the stirred white suspension at −50° C. using a metering pump. The resulting reaction mixture was quenched with 100 mL of water, the organic phase separated, the aqueous phase was extracted twice with 100 mL diethyl ether, and the diethyl ether extracts combined. The combined diethyl ether extracts were dried over sodium sulfate, filtered, and the diethyl ether solvent was removed under reduced pressure to provide 89.82 g (0.303 mol, 89% yield) of the above-titled mixture in a ratio of 93.9:6.1 as determined using HPLC.

Example 2
Synthesis of a Mixture of Tramadol and its Corresponding Trans Isomer in a Ratio of About 92:8

To 230 mL of anhydrous tetrahydrofuran (THF) cooled to −60° C. was added 9.36 g of n-butyl lithium (0.123 mol, 10 M solution in hexanes). The resulting yellow solution was stirred for 10 min and then 23.06 g of neat 3-bromoanisole (0.34 mol) was added dropwise with stirring. The resulting white suspension was stirred for 15 min. To the white suspension was then added dropwise, over a 4 hour period, a solution of 19.14 g of (±) 2-((dimethylamino)methyl) cyclohexanone (0.123 mol) and 400 mg of iron (III) chloride (2.5 mmol, 2 mol percent) in 190 mL of anhydrous THF at −60° C. The resulting reaction mixture was quenched with water, the organic phase was separated, the aqueous phase was extracted twice with diethyl ether and the diethyl ether extracts were combined. The combined ether extracts were dried over sodium sulfate, filtered, and the solvent was removed under reduced pressure to provide 37.77 g (0.084 mol, 68% yield) of the above-titled mixture in a ratio of 91.9:8.1 as determined using HPLC.

Example 3
Synthesis of a Mixture of Tramadol and its Corresponding Trans Isomer in a Ratio of About 98:2

To a solution of 3.53 g of (±)-2-((dimethylamino)methyl) cyclohexanone (23 mmol) dissolved in 20 mL of THF at 0° C. was added dropwise a solution of 37 mg of iron (III) chloride (0.2 mmol, 1 mol percent) in 3 mL of THF at 0° C. The resulting violet solution was cooled to −78° C. In a separate vessel, 5.10 g of 3-bromoanisole (27 mmol) was dissolved in 50 mL of THF and the resulting solution was cooled to −78° C. To the solution of 3-bromoanisole was added dropwise with stirring 2.07 g of n-butyl lithium (27 mmol, 10 M solution in hexanes). The resulting white suspension was stirred for 1 hour and then transferred dropwise over a 4 hour period to the solution of (±) 2-((dimethylamino)methyl) cyclohexanone and iron (III) chloride at −78° C. The reaction mixture was quenched with water, the organic phase was separated, the aqueous phase was extracted three times with diethyl ether and the diethyl ether extracts were combined. The combined ether extracts were dried over sodium sulfate, filtered, and the solvent was removed under reduced pressure to provide 6.92 g (14 mmol, 62% yield) of the above-titled mixture in a ratio of 97.8:2.2 as determined using HPLC.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference in their entireties.

What is claimed is:

1. A composition comprising (±)-2-((dimethylamino)methyl)cyclohexanone, a transition-metal salt, and an organic solvent.

2. The composition of claim 1, wherein the transition-metal salt is $FeX_2$, $FeX_3$, $FeX_4$, $FeX_6$, $SnX_4$, $SnX_2$, $ZnX_2$, $CuX$, $CuX_2$, $TiX_4$, $MnX_2$, $MnX_3$, $MnX_4$, $MnX_6$, $MnX_7$, $NiX_2$, or a mixture thereof, and X is chloride, bromide, iodide, or fluoride.

3. The composition of claim 2, wherein X is chloride or bromide.

4. The composition of claim 1, wherein the organic solvent is benzene, toluene, xylene, pentane, heptane, hexane, cyclohexane, ligroin, petroleum ether, diethyl ether, tetrahydrofuran, dioxane, or a mixture thereof.

5. The composition of claim 4, wherein the organic solvent is substantially anhydrous.

6. A composition comprising: (a) a complex formed between a transition-metal salt and (±)-2-((dimethylamino)methyl)cyclohexanone; and (b) an organic solvent.

7. The composition of claim 6, wherein the transition-metal salt is $FeX_2$, $FeX_3$, $FeX_4$, $FeX_6$, $SnX_4$, $SnX_2$, $ZnX_2$, $CuX$, $CuX_2$, $TiX_4$, $MnX_2$, $MnX_3$, $MnX_4$, $MnX_6$, $MnX_7$, $NiX_2$, or a mixture thereof, and X is chloride, bromide, iodide, or fluoride.

8. The composition of claim 7, wherein X is chloride or bromide.

9. The composition of claim 6, wherein the organic solvent is benzene, toluene, xylene, pentane, heptane, hexane, cyclohexane, ligroin, petroleum ether, diethyl ether, tetrahydrofuran, dioxane, or a mixture thereof.

10. The composition of claim 9, wherein the organic solvent is substantially anhydrous.

11. A complex formed between a transition-metal salt and (±)-2-((dimethylamino)methyl)cyclohexanone.

12. The complex of claim 11, wherein the transition-metal salt is $FeX_2$, $FeX_3$, $FeX_4$, $FeX_6$, $SnX_4$, $SnX_2$, $ZnX_2$, $CuX$, $CuX_2$, $TiX_4$, $MnX_2$, $MnX_3$, $MnX_4$, $MnX_6$, $MnX_7$, $NiX_2$, or a mixture thereof, and X is chloride, bromide, iodine, or fluoride.

13. The complex of claim 12, wherein X is chloride or bromide.

* * * * *